United States Patent [19]

Dao et al.

[11] Patent Number: 5,760,165

[45] Date of Patent: Jun. 2, 1998

[54] BISALLYLOXYIMIDES

[75] Inventors: Buu Dao, Lalor; Trevor Morton, Aspendale, both of Australia

[73] Assignee: Commonwealth Scientific and Industrial Research Organization (CSIRO), Victoria, Australia

[21] Appl. No.: 851,855

[22] Filed: May 6, 1997

Related U.S. Application Data

[62] Division of Ser. No. 550,153, Oct. 30, 1995, abandoned.

[30] Foreign Application Priority Data

Oct. 28, 1994 [AU] Australia ............ PM9109/94

[51] Int. Cl.[6] .................................. C08G 73/10
[52] U.S. Cl. .................. 528/322; 528/310; 528/327; 528/330; 548/433; 548/461; 548/475
[58] Field of Search .................. 528/322, 310, 528/327, 330; 548/433, 461, 475

[56] References Cited

U.S. PATENT DOCUMENTS

| | | | |
|---|---|---|---|
| 3,444,184 | 5/1969 | Petropoulos et al. | 528/322 |
| 4,440,566 | 4/1984 | Luo | 528/310 |
| 4,927,899 | 5/1990 | Michaud et al. | 528/310 |
| 5,306,718 | 4/1994 | Lauffer et al. | 514/230.8 |
| 5,346,911 | 9/1994 | Augeli-Szafran et al. | 528/322 |

FOREIGN PATENT DOCUMENTS

| | | |
|---|---|---|
| 0 272 210 | 6/1988 | European Pat. Off. . |
| 0 273 839 | 7/1988 | European Pat. Off. . |
| 0 368 225 | 5/1990 | European Pat. Off. . |
| 0368225A1 | 5/1990 | European Pat. Off. . |
| 0456089A1 | 11/1991 | European Pat. Off. . |
| 1331203 | 9/1973 | United Kingdom . |

OTHER PUBLICATIONS

Chemical Abstracts 103: 6220p, p. 561, 1985.
Chemical Abstracts 102: 24109t, p. 645, 1985.
Furdik, et al., *Chemical Abstracts*, vol. 71, No. 21, 24 Nov. 1969, 101385a.

Kim et al., *Chemical Abstracts*, vol. 117, No. 1, 3 Aug. 1992, 48268e.

Perjessy et al., *Chemical Abstracts*, vol. 109, No. 17, 24 Oct. 1988, 148780u.

Kogyo, *Chemical Abstracts*, vol. 103, No. 1, 8 Jul. 1985, 6220p.

Khachaturyan, *Chemical Abstracts*, vol. 81, No. 11, 16 Sep. 1974, 62716u.

*Primary Examiner*—Joseph McKane
*Attorney, Agent, or Firm*—Bacon & Thomas

[57] ABSTRACT

Monoallyloxyimides, diallyloxyimides and polyallyloxyimides of general Formula I.

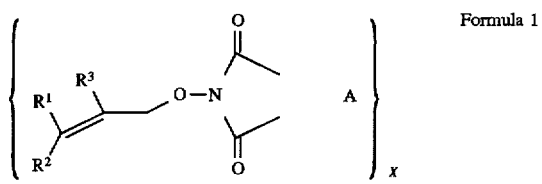

Formula 1 wherein:

X is an integer from 1 to 4 inclusive;

$R^1$, $R^2$, and $R^3$ are independently selected from the group comprising hydrogen, alkyl, arylalkyl or halogen; and A is all or part of an aromatic, alicyclic or mixed aromatic/ alicyclic ring system optionally substituted with one or more alkyl, alkoxy, alkylthio, aryl, heteroaryl, aryloxy, carboxy, alkylamino, dialkylamino, amino, nitro, cyano, halo or haloalkyl groups.

This new class of reactive monomer can be used as co-reactants in themosetting matrix resins. The reactive monomers, either alone or with other comonomers, can give rise to cured resin matrix materials with high thermal stability. Mixed with suitable bismaleimide monomers, they can be cured into useful composites having substantially improved thermal stabilities.

6 Claims, No Drawings

BISALLYLOXYIMIDES

This application is a Division of application Ser. No. 08/550,153, filed Oct. 30, 1995, now abandoned.

This invention relates to a new class of reactive monomer which can be used as a co-reactant in thermosetting matrix resins. The new materials offer a number of advantages over the commonly used co-reactants including improved thermal stability, higher Tg and in some cases better resin flow properties. The reactive monomers, either alone or with other comonomers, can give rise to cured resin matrix materials with high thermal stability. When these new materials are mixed with suitable bismaleimide monomers, either commercially available or experimental, and applied to suitable reinforcing fibres such as carbon, they can be cured into useful composites having substantially improved thermal stabilities as judged from thermal weight loss at 250° C. and 204° C. The invention also includes polymers and copolymers of the reactive monomers and composites and other products comprising them. The invention further includes methods of synthesis of the reactive monomers.

Bismaleimide monomers have been used to make thermosetting polyimides for a number of years. Compared to other polyimide thermosets, bismaleimides offer the advantage of having processing and curing requirements closest to those of high performance epoxy systems and in view of their generally higher thermal stability compared to epoxies, have been attractive for advanced composite and other applications requiring higher temperature capability than epoxies. However as the uses of advanced composite systems have expanded into higher temperature applications even conventional bismaleimide systems are inadequate and to some extent interest has been focussed on other thermosetting systems such as either the PMR systems, or norbornenyl, phenylethynyl and styryl end-capped systems. In all of the high temperature matrix resins a major problem has been to balance the requirements for good flow and low melting point of the uncured resin needed for easy processability with the need for a highly aromatic final structure with good oxidation and thermal resistance. Another problem with the early bismaleimide systems was their inherent brittleness, resulting from the relatively low molecular weight of the monomers used and the facility with which the bismaleimide polymers themselves self polymerise, factors which lead to a high degree of cross-linking. This latter facet of bis: leimides has been addressed in International Patent Application No. PCT/AU93/00248 which describes high molecular weight bismaleimides.

The versatile chemistry of the maleimide moiety permits reaction with a range of property modifying substances to make co-polymers of great use as resin matrices. The maleimide double bond is electron deficient and highly reactive to nucleophiles. Thus amines, hydrazides and thiols readily undergo a Michael type addition across the double bond to give substituted succinimides. Dienes can undergo Diels-Alder addition with the maleimide double bond to give fused six member ring structures in the polymer chain which can often be aromatised. Olefinic compounds can undergo an ene addition reaction and cyanates are thought to add in a trimolecular reaction to give a suggested maleidopyrimidine structure. There are representatives of all these classes of co-reactant in the prior art.

Perhaps the most developed cure chemistry in use with bismaleimides is their co-reaction with bisallylic phenols of various types using ene curing chemistry. These can be as simple as 3,3'-diallylbisphenol A as used in the Matrimid™5292 commercial bismaleimide system or larger molecular weight materials such as the bis [2-allylphenoxy] phthalimides developed by Stenzenberger and Konig (1989), High Performance Polym., 1,133.

The curing of any of these materials to produce the final product is thought to involve, initially, ene reactions to produce aryl/alkenyl dienes which can then undergo further reaction with maleimide by Diels-Alder additions. The partially aromaticized structure resulting, appears to limit the thermo-oxidative stability of the matrix, so that typically, a laminate made from such a system could lose from 4–10% of its weight on thermally aging at 204° C. for six months. Similar laminates made with the co-reactants that are the subject of this claim typically lose less than 2% in weight under the same conditions.

There is a fairly extensive literature on the use of bisallylimides as resin precursors. Thus N,N'-diallyl-2,3,3', 4'-biphenyltetracarboxylic diimide was claimed in JP81/118, 061 as a precursor of the corresponding diglycidyl derivative. However the present invention is concerned with bisN-allyloxyimides.

There is only a meagre literature on allyloxyimides. Most allyloxyimides reported in the literature have either been used as synthetic intermediates in the preparation of allyloxyamine or have been synthesised for screening for biological activity. Diallyloxyimides are unknown in the scientific literature.

In one aspect, this invention provides monoallyloxyimides, diallyloxyimides and poiyallyloxyimides of general Formula I.

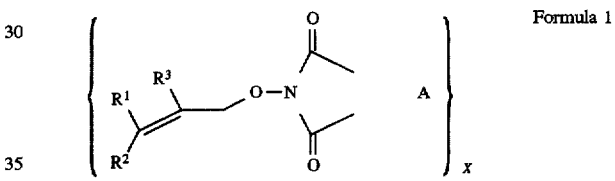

Formula 1 wherein:

X is an integer from 1 to 4 inclusive;

$R^1$, $R^2$, and $R^3$ are independently selected from the group comprising hydrogen, alkyl, arylalkyl or halogen; and A is all or part of an aromatic, alicyclic or mixed aromatic/alicyclic ring system optionally substituted with one or more alkyl, alkoxy, alkylthio, aryl, heteroaryl, aryloxy, carboxy, alkylamino, dialkylamino, amino, nitro, cyano, halo or haloalkyl groups.

For Example, when X=2, A may be port of a benzene ring, forming compounds typified by Formula 2 or it may be part of a larger fused aromatic system such as naphthalene anthracene, etc.

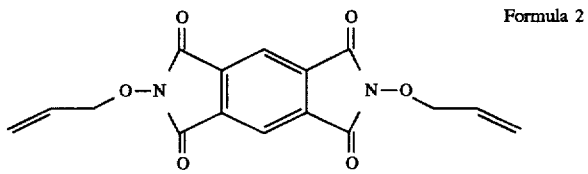

Formula 2

Alternatively A can be a larger structural entity containing one or more aromatic rings. In this case A can be part of an optionally substituted aryl, bridged or bonded di- or polyaryl (an example is the 2,2-bis[4-phenyleneoxyphenyl] propane moiety) or heteroaryl group. The aryl groups may be substituted with one or more alkyl, alkoxy, alkylthio, aryl, heteroaryl, aryloxy, carboxy, alkylamino, dialkylamino, amino, nitro, cyano, halo or haloalkyl groups.

A further alternative is for A to be part of an alicyclic system as in for example N-allyloxynadimide or a mixed aryl/alicyclic system.

The alkenoxy bearing imide section is usually a five-membered ring as depicted in Formula I but can be six-membered as in 1,8- and 4,5-naphthoic imides or even seven-membered. There may be additional imide groups such as maleimido or nadimido in the molecule. Nadimide is bicyclo[2.2.1]heptane-2,3-dicarboxylic imide.

Throughout this specification:

"Aryl" means an aromatic carbocyclic group, such as phenyl, naphthyl, and the like.

"Bridged or bonded di- or poly- aryl" means a group consisting of two or more aromatic carbocyclic ring systems, such as phenyl, naphthyl or the like joined by a bond, such as in biphenyl, or a bridging group, such as in sulphonyldiphenyl. Bonding between rings may also be by way of a carbon-to-nitrogen bond such, as in aryl substituted imides.

"Bridging group" includes for example $SO_2$, CO and O such as in compounds of the formula (IIIa)

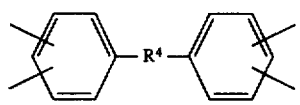

IIIa wherein $R^4$ is a divalent radical such as $SO_2$, CO and O.

"Heteroaryl" means aromatic monocyclic or polycyclic groups containing at least one hetero atom such as nitrogen, oxygen or sulfur. Examples of suitable "heteroaryl" groups are:

3- to 8-membered, more preferably 5- or 6-membered heteromonocyclic groups containing 1 to 4-nitrogen atom(s), for example, pyrrolyl, imidazolyl, pyrazolyl, pyridyl, pyrimidyl, pyrazinyl, pyridazinyl, triazinyl; condensed heterocyclic groups containing 1 to 5 nitrogen atom(s), for example, indolyl, isoindolyl, indolizinyl, benzimidazolyl, quinolyl, isoquinolyl, indazolyl, benzotriazolyl, etc.;

3 to 8-membered heteromonocyclic groups containing 1 or 2 sulfur atom(s) and 1 to 3 nitrogen atom(s), for example, thiazolyl, isothiazolyl, thiadiazolyl, etc.; 3 to 8-membered heteromonocyclic groups containing 1 or 2 sulfur atom(s), for example thienyl, etc.; condensed heterocyclic groups containing 1 or 2 sulfur atom(s) and 1 to 3 nitrogen atom(s), for example, benzothiazolyl; benzothiadiazolyl, etc.; 3 to 8-membered heteromonocyclic groups containing an oxygen atom, for example, furyl, etc.; condensed heterocyclic groups containing 1 to 2 sulfur atom(s), for example, benzothienyl, etc.; and condensed heterocyclic groups containing 1 or 2 oxygen atom(s), for example, benzofuranyl, etc.

"Alkyl" groups may be straight chain or branched and contain 1–20 carbon atoms. Suitable alkyl groups are methyl, ethyl, propyl, iso-propyl, n-butyl, iso-butyl, tert-butyl, n-pentyl, iso-pentyl, neo-pentyl, n-octyl, iso-octyl, decyl, cetyl, stearyl, and the like.

The terms "alkoxy" and "alkylthio" mean groups in which the alkyl moiety is a branched or unbranched saturated hydrocarbon group containing from one to eight carbon atoms bonded to an oxygen or sulphur.

"Alicyclic" means saturated cyclic or polycyclic groups.

"Alkanoyl" means groups of the formula R—CO where R is an alkyl group. Examples are formyl, acetyl, propionyl, butyryl, valeryl, iso-valeryl, pivaloyl, hexanoyl, and the like.

"Alkenyloxy" means such groups in which the alkenyl moiety is a branched or unbranched unsaturated hydrocarbon group containing from two to eight carbon atoms, such as vinyl, allyl, propenyl, crotonyl, bonded to an oxygen atom.

According to a further aspect, this invention provides a method of making a compound of Formula 1 which comprises reacting a compound of Formula 4 with an oxime of Formula 5, wherein A, $R^1$, $R^2$, $R^3$ and X are as defined above; and Z is a reactive atom or group, preferably a halogen atom.

The compounds of Formula 5 may be produced by any suitable method, for example by reacting the corresponding acid anhydride with hydroxylamine.

Formula 4

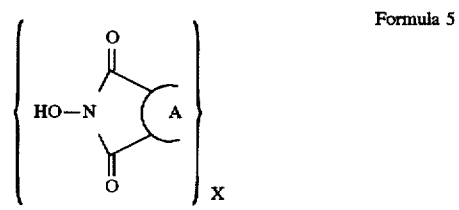

Formula 5

According to a still further aspect of this invention there is provided a curable resin formulation, characterised in that it contains a compound of the Formula 1 defined above. The formulation may contain other additives such as toughening agents, flow promoters, fluxing agents.

In a preferred version such a curable formulation may contain at least one bismaleimide monomer, whether a commercially available material or any of a number of experimental bismaleimide monomers such as those which are the subject of PCT/AU93/00248 or any mixture of bismaleimide monomers both commercial and experimental. Preferably there should be at least 1 equivalent of bismaleimide to each equivalent of allyloxyimide.

A curable resin is one which can be converted to a polymeric structure by the application of heat, UV irradiation, microwave irradiation, electron beam and other related irradiation techniques.

Compounds of Formula 1 will also self polymerise at temperatures around 300° C. A further aspect of this invention is the use of this property to produce monomers with a suitable end capping capable of thermal polymerisation. A preferred compound for this application is an oligoimide material which is end terminated with allyloxyimide end groups.

Compounds of Formula 1 will also copolymerise with norbornyl capped imide compounds and act as reactive plasticisers.

The curable formulations listed above can be used to make polyimides for a variety of applications including adhesives for materials including metals particularly those known to the aerospace industry such as aluminium alloy and titanium; machinable polyimide bar stock material; films, electronic encapsulation, circuit board materials and other related uses, moulded components and composites including composite tooling.

In another aspect, the present invention provides for reactive monomer additives which have low melting points and hence good flow enhancing properties even when part of highly aromaticized, and hence heat stable, structures. For example small amounts of some of these materials when admixed with other polyimide materials can aid processing or elevate Tg of the final product.

The curable formulations of the invention may be applied to reinforcing cloth such as unidirectional or woven carbon fibre either from solution (preferably from a halogenated hydrocarbon or other volatile solvent); from a suspension; from a hot melt or by a powder prepregging technique. Application may be manual or by a machine process including those involving transfer from a precoated transfer medium.

In another aspect, the present invention provides an impregnated fibre reinforced material (commonly known as a "prepreg") characterised in that the fibre reinforcements are impregnated with a curable formulation as defined above.

The impregnated fibre materials can be laid down by any suitable known method for making composite materials such as, for example, vacuum bagging on a caul plate or an appropriate tool or hot pressing.

The impregnated fibre reinforced materials are suitable for use in the production of advanced composite materials.

Thus in a further aspect, the present invention provides a composite material comprising a fibrous material in a matrix of a cured formulation in accordance with the invention defined above.

Alternatively, the compounds of the invention can be used in an appropriate resin formulation for resin transfer moulding or for the manufacture of sheet moulded material. Another envisaged application is in pultrusion.

The invention is illustrated by the following non-limiting examples. In the descriptions below the systematic names are based on Chemical Abstracts names of related compounds. However, because of the difficulty of systematically naming these structures, names given are not to be taken as conclusive of the structure of the materials of this invention, but rather the compounds of this invention are defined by Formula 1.

The following terms and abbreviations are used in the Examples:

Ultemanhydride is 2,2-bis-[4-(3,4)-dicarboxyphenoxy) phenyl]-propanedianhydride. It has the structure:

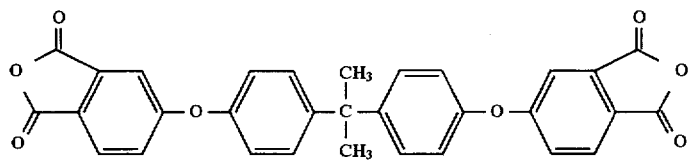

DDS/Red.BTDA DABI is the diamine-bisimide formed from 4,4'-diaminodiphenyl sulphone (DDS) and reduced benzophenone tetracarboxylic acid anhydride (Red.BTDA). It has the structure:

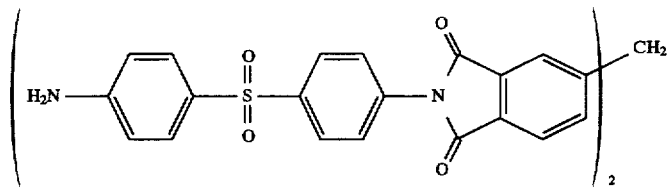

DABCO is 1,4-diaza bicyclo[2.2.2]octane.
DMAC is dimethylacetamide.
DSC stands for Differential Scanning Calorimetry.
GPC stands for Gel Permeation Chromatography.
DTMA stands for Dynamic Mechanical Thermal Analysis.
6-FDA is 2,2-bis[4-(3,4-dicarboxy phenyl)hexafluoro] propane dianhydride.

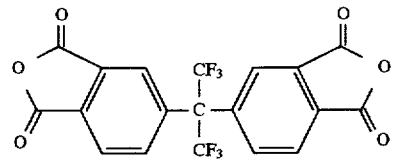

EXAMPLE 1

2,6-diallyloxybenz[1,2-c:4,5-c']-dipyrrole-1,3,5,7(1H,6H)-tetrone Formula 2

(Formula I. A=1/2[1,2,4,5-phenylene]) X=2,$R^1$, $R^2$, $R^3$=H

A solution of hydroxylamine hydrochloride (107 g, 1.54 mole) in pyridine (1l) in a three-necked flask fitted with thermometer, mechanical stirrer, reflux condenser and blanketed with argon was cooled to 30° C. and pyromellitic anhydride (152.7 g, 0.7 mole) was added. The mixture was stirred at room temperature for 10–15 minutes during which the exotherm raised the temperature from 30°–45° C. The mixture was then heated to 90° C. for 45 min. At the end of this time, the reaction mixture is cooled and the fine precipitate was filtered off, washed with water (the red anion is present in basic aqueous medium), dilute acetic acid and once more with water to yield the bis-hydroxy compound (dihydroxypyromellitimide) as a cream powder, mp 300°–303° C., 11.7 g (64.3%).

The dihydroxypyromellitimide (74.4 g, 0.3 mole) in a mixture of dry DMF (300 ml) and triethylamine (0.6 mole, 83.7 ml) was stirred at room temperature. Then allyl bromide (87.12 g, 62.33 ml, 0.72 mole) was added in one lot and a solution was attained. The temperature rose to 45° C. The initial red colour of the anion was dispelled after about 10 minutes and a fine precipitate formed. The mixture was usually left to stir overnight. At the end of this time, the reaction mixture was cooled in ice for 30 min and the precipitate was filtered off and then washed with water and then cold methanol; the title compound was obtained on drying (64 g 67%).

Pure N,N'-Diallyloxypyromellitimide was obtained by recrystallisation from dichloromethane/light petroleum as colourless needles, mp 222°–223° C. Mass spectrum (c.i.) 329 (M+1), 357 (M+29). $^1$H nmr (CDCl3): 4.73, m, 4H; 5.34, m, 2H: 5.42, m 2H; 6.11, m, 2H; 8.26, s, 2H.

EXAMPLE 2

Preparation 2,2-bis[2-allyloxy-1,3- dihydro-1,3-dioxo-2H-isindolyloxyphenyl]propane (Bisallyloxyimide of ultem anhydride). (Formula I, A=1/2 {2,2-bis[3- and 4-phenyleneoxyphenyl]propane}, X=2, $R^1$, $R^2$, $R^3$=H A solution of hydroxylamine hydrochloride (30.6 g, 0.44 mole) in pyridine (300 ml) in a three-necked flask fitted with thermometer, mechanical stirrer, reflux condenser and blanketed with argon was cooled to 30° C. and ultem anhydride (106 g, 0.2 mole) was added. The mixture was stirred at room temperature for 10–15 minutes during which the exotherm raised the temperature from 30°–45° C. The mixture was then heated to 90° C. for 45 min. At the end of this time, the reaction mixture was cooled to room temperature and poured into water. An oil formed, most of which could be decanted. A second lot of oil was collected on further settling. The combined oil was redissolved in $CH_2Cl_2$ with the aid of a little methanol and washed twice with water. After drying with $NA_2SO_4$ and evaporation, the bis-hydroxy compound (dikydroxyultemimide) was obtained as an off-white powder, mp 81°–83° C., 120 g (98%).

The dihydroxyultemimide (42 g, 0.075 mole) in dry DMF (200 ml) and triethylamine (0.15 mole, 15.3 g, 21 ml) was stirred at room temperature. The solution became dark red. Allyl bromide (22.01 g, 15.75 ml, 0.18 mole) was added in one lot and after 5–10 min reaction time, the mixture had lightened from dark red to orange and a fine precipitate had formed. The stirring was continued overnight and at the end of this time had become light yellow. The reaction mixture was poured into water and the product filtered off. On redissolution in dichloromethane and washing twice with water, evaporation yielded the N,N'-Diallyloxyultemimide , mp 150°–152° C., (30 g, 64%). Mass spectrum (c.i.) 631 (M+1), 659 (M+29). $^1$H nmr (CDCl$_3$): 1.78,s, 6H; 4.69, m, 4H; 5.39,m,4H; 6.11,m,2H; 7.01, m, 4H; 7.30,m 8H; 7.77, m,2H.

EXAMPLE 3

Preparation 2,2-bis[2-allyloxy-1,3-dihydro-1,3-dioxo-2H-isoindolylphenyl]hexafluoropropane (Bisallyloxyimide from 6-FDA) (Formula , A=1/2 {2,2-bis[phenyl] hexafluoropropane }, X=2, $R^1$, $R^2$,$R^3$=H)

Synthesis using a similar method to examples 1 and 2 above, yielded, in two steps, the N,N'-Diallyloxy-6-F-Diimide as colourless crystals, mp 58°–60° C. in 48% overall yield. Mass spectrum (c.i.) 555 (M+1), 569 (M+15), 583 (M+29). $^1$H nmr (CDCl$_3$): 4.71,m, 4H; 5.37,m, 2H, 5.44,m, 2H; 6.10, m, 2H, 7.78, m, 7.82, m, 4H; 7.90, m, 7.94, m. 2H.

EXAMPLE 4

Preparation N,N'-diallyloxyimide from an oligoimide dianhydride made from reaction of pyromellic anhydride and DDS/RedBTDA DABI.

The DDS/Red.BTDA DABI was made by a method similar to the one described in Section 2.7.1 in the paper: Hawthorne, D. G., Hodgkin, J. H., Jackson, M. B., Loder, J. W. and Morton. T. C., (1994), High Perform. Polymers, 6, (4). The DDS/Red.BTDA DABI (10.56 g, 0.015 mole) and DABCO (2.53 g, 0.0225 mole) were dissolved in dry DMAc (70 ml). The solution was outgassed with argon and heated to 130° C. Then a solution of pyromellitic anhydride (6.544 g, 0.03 mole) in dry DMAc (50 ml) was added slowly in order to maintain the reaction temperature at 130° C. After the addition, toluene (50 ml) was added and the reaction temperature was raised to achieve reflux. Water produced in the reaction was removed by means of a Dean and Stark separator. After 10 h the mixture was cooled and the product collected by pouring the reaction mixture into acetone. The precipitate was stirred for 10 minutes and then filtered off. The product was resuspended in acetone and filtered off once again, and then dried (1 1.5 g). This product was suspended in acetic anhydride, stirred mechanically and heated to 110° C. for 1 h. On cooling the solid oligoimide anhydride was filtered off, and washed with toluene and then acetone and dried under vacuum (10 g). $^1$H nmr (D6-DMSO): 4.41, bs, CH2, 2H; 7.75, m, 7.91, m, 8.0,m, 16H; 8.17, m, 10H; 8.42,s, 8.60, m, 2H.

This oligomer anhydride was then was converted to N-allyloxyimide end-capped material by a method similar to that in examples 1 and 2 above to yield in two steps, the crude N,N'Diallyloxyoligoimide as a buff solid, mp (DSC) 110° C., 5.16g (40% yield from the anhydride). GPC showed that this material contained 48% of the required 2:1 adduct. $^1$H nmr (CDCl$_3$): 2.64, bs, H2); 4.18, s, 4.26,s, CH2 (2 species), 4.9H; 4.63, m, 7.3H; 5.32, m, 6.9H; 6.05,m,2H; 6.63, m, 6H; 7.62,m, 27.6H; 7.96,m, 8.3H.

The nominal structure of the product is:

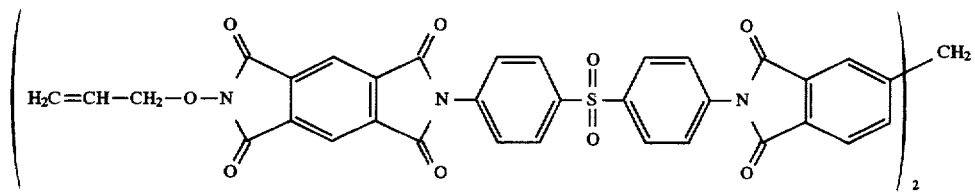

EXAMPLE 5

N,N'-Diallyloxy-1,4,5,8-naphthalene tetracarboxylic-1,8:4,5-diimide (Formula I A=1.8:4,5 naphthalene, X=1, $R^1$, $R^2$, $R^3$=H)

1,4,5,8-Naphthalene tetracarboxylic dianhydride (13.41 g, 0.05 mole) was added to a solution of hydroxylamine hydrochloride (6.95 g, 0.01 mole) in pyridine (100 ml) according to the conditions described in Example 1. The cooled reaction mixture was poured into water and the precipitate that formed was filtered off. The product was washed by suspension in 2:1 acetic/ water, filtered, and washed by suspension again in water.

After drying, the crude product above was dissolved in dry DMF (80 ml) and treated with allyl bromide (14.52 g, 0.12 mole, 20% excess). After stirring overnight and work up as in Example 1, the allyloxyimide was obtained as a buff coloured solid, m.p 270° C. decomp. (15.65 g, 82%). $^1$H nmr (CDCl$_3$/D4—MeOH—) δ8.68, m, 4H; 6.06,m, 2H; 5.24, m, 4H; 4.68, d, 4H.

EXAMPLE 6

N-Allyloxy-1,8-naphthalene dicarboximide (Formula I A=1, 8: naphthalene, X=1, $R^1$, $R^2$, $R^3$=H)

The two step procedure described in Example 1 yielded this product as a white crystalline solid, m.p. 138°–140° C. (5.94 g, 53.5 %). $^1$H nmr (CDCl3) δ8.64, d, 2H; 8.25, d, 2H; 7.88, m, 2H; 6.21, m, 1H; 5.37, m, 2H; 4.80, m, 2H.

EXAMPLE 7

4-[2-Allyloxy-1,3-dioxo-2H-isoindolyl-4-oxy]phenyl nadimide(Formula I A=phenyleneoxyphenylnadimide X=1, $R^1$, $R^2$, $R^3$=H)

A 4-Hydroxyphenylnadimide

Nadic anhydride (98.4 g, 0.06 mole), p-aminophenol (65.4 g, 0.6 mole) and DABCO (92.55 g,0.02283 mole) in dry DMF (400 ml) were refluxed under argon for 3 h over which time a small amount of distillate was removed via a Dean and Stark collector. On cooling and then pouring into water the product was precipitated as a brown powder After filtering and washing with water the product was dried to give 4-hydroxyphenylnadimide (138.7g, 90%). $^1$H nmr (CDCl3/DMSO) δ6.73,m, 4H; 6.11, s, 2H; 3.30, m, 4H; 1.55, m, 2H.

B N-allyloxy-4-ntrophthalimide

Caution. Care should be taken in using hydroxylamine hydrochloride in acetic acid at 90° C.

Hydroxylamine hydrochloride (6.95 g, 0.11 mole) in glacial acetic acid (200 ml) was stirred magnetically at 60° C. until most of the solid was in solution (15 min). 4-Nitrophthalic anhydride (19.3 g, 0.1 mole) was added in portions and then the reaction mixture raised to 90° C. Stirring was continued at 90° C. for 8 h. Cyclohexane (40 ml) was added and part of the cyclohexane/acetic was allowed to distil via a Dean and Stark collector. After 6 h the flask was cooled. The solution was decanted from a small amount of solid material and reduced to dryness on the rotary evaporator. Water was added and the pH adjusted to 7 with $NaHCO_3$. The solid which had precipitated out was filtered and washed once with water. The product was dried in vacuum overnight at 60° C. to give a yellow solid (7.27 g, 35%).

The product above was converted to the N-allyloxy derivative by a procedure similar to that in Example 1. Yellow solid (7.34 g, 85%). $^1$H nmr (CDCl3) δ8.63,m, 2H; 8.05,dd, 1H; 6.12, m, 1H; 5.38,m, 2H; 4.74,dd, 2H.

The N-allyloxyimide is easily reduced to N-allyloxy-4-aminophthalimide by standard iron powder reduction such as described by Fox and Threlfall in Org. Synthesis, Coll. Vol. V, p347. This compound is an important intermediate for insertion of the N-allyloxyphthalimido end grouping into polyimides C Nitro displacement reaction Hydroxyphenylnadimide (10.66 g, 0.0418 mole) suspended in dry methanol (150 ml) was treated with sodium methoxide (2.483 g, 0.046 mole). The mixture was stirred at room temperature for 1 h during which time a solution was obtained. The methanol was removed on the rotary evaporator and the residue triturated with dry benzene followed by re-evaporation, several times. Finally the sodium salt was left under high vacuum at 50°–60° C. for 30 min. The sodium salt was redissolved in dry DMF (100 ml) and brought to 80° C. and then the N-allyloxy-4-nitrophthalimide (10.37 g, 0.0418 mole) was added in one lot. The mixture was stirred at 80° C. for 4 h.

The volume of the reaction mixture was reduced to half on the evaporator and then he residue poured into water. The grey precipitate was filtered off, washed, and dried. Extraction of the aqueous filtrate with ether yielded a small amount of unchanged hydroxyphenylnadimide. The dried product was dissolved in dichloromethane and the solution clarified by filtering through celite. On evaporation the residue was triturated with methanol to remove further unchanged hydroxyphenylnadimide and the residual product filtered off to yield a light grey powder, (5.42 g, 28%). This material was recrystallised from $CH_2Cl_2$/Light petroleum to give white crystals, m.p.210° C. (DSC). Mass spectrum: m/z 457 (M+1, 100%), 485 (M+29, 13%), 497 (M+41,6%). $^1$H nmr ($CDCl_3$) δ7.83,d, 1H; 7.4-7.1,m, 6H; 6.28, s, 2H; 6.15, m, 1H; 5.33,m, 2H, 4.69,dd, 2H; 3.49, m, 4H; 1.72, m, 2H plus $H_2O$.

This material showed a DSC exotherm peak at 337° C., yielding 221 kJ/mole.

EXAMPLE 8

Preparation of Cured Neat Resin Bars

This procedure is one of a number of alternative procedures used: An experimental bismaleimide (Example 5 of PCT/AU93/00248) (23.17 g, 0.027 mole) was preheated in an oil bath at 180° C. under vacuum for 30 min. The bisallyloxyimide compound from example 1 above (8.83, 0.027 mole) was preheated under vacuum for 15 min. in an oil bath at 150° C. and then the temperature of the bath was raised to 190° C. and the bismaleimide gradually blended into the softening mass. CAUTION reaction exotherm starts at higher temperatures. The temperature of the bath was eventually raised to 220°–230° C. to complete the blending. Oil pump vacuum (1–2 mmHg) was applied for 10 min and then the mix was either directly transferred into a preheated mould or cooled, ground to a powder and compressed into a mold on the hot press. Best results were obtained in this case by a cure at 220° C. for 6 h, followed by a post cure of 3 h at 280° C. Samples obtained in this way were not entirely free of voids but were suitable for DMTA testing. Tg (1 Hz) 311° C.

EXAMPLE 9

Preparation of Laminates

Because of limited solubility of the experimental bismaleimide it was necessary to micropulverize the resin mix and apply as a suspension.

The bismaleimide used in Example 8 above was preheated to remove volatiles and the heated in an oil bath held at 190° C. The bisallyloxyimide compound from example 1 above (3.20 g, 0.0098 mole) was added in portions to the bismaleimide (9.89 g, 0.0115 mole) held at 190° C. The temperature of the oil bath was brought to 210°–220° C. and the reaction mixture degassed by application of vacuum. On cooling the solid product was ground up and then micropulverized with dichloromethane to give a suitable mixture for prepregging. SP Systems RC200P plain weave carbon fibre cloth or equivalent was coated at a rate of 1.1 g of resin/g of cloth. The prepregs were dried in warm air for 60 min and "B" staged at 110° C. for 2–5 min. A 10×10 cm coupon for DMTA use was typically made by aligning 5 plies of prepreg in the warp direction and hot pressing between caul plates under a low initial pressure of a few psi until the platens reached 220° C., followed by 46 psi at 220° C. for 1 h, increasing to 115 psi as the temperature is raised to 250° C. for 2 h and then finally 280° C. for 2 h. Table 1 gives some properties of laminates made in this way.

TABLE 1

Summary of some Properties of Selected Experimental Bismaleimides cured with Bisallyloxyimides of Examples 1 and 4

|  | BMI (Example 5)/ Matrimid ™ 5292B | BMI (Example 5)/ Compound of example 1 | BMI 2 Experimental/ Compound of example 1 | BMI (Example 5)/ Bisallyloxy compound of example 4 |
|---|---|---|---|---|
| Tg °C. (aver.) | 269 (226) | 265 (222) | 304 (272) | 280 (245) |
| Tg (wet) 7D at 71° C. | 246–241 (170) | 275–269 (233) | na | |
| Thermal Stab Wt. loss @ 250° C. 1D, 7D, 14D | 0.51, 1.62, 2.40 | 0.32, 0.73, 1.11 | na, 0.85, 2.37 | 0.19, 0.24, 0.61 |
| Thermal Stab Wt loss @ 204° C. 1M, 3M, 6M | 0.82, 1.89, 3.67 | 0.16, 0.77, 1.63 | 0.14, 1.63, 5.81 | |
| Water uptake % @ 71° C. 1D, 7D, 14D | 1.04, 1.53, 1.63 | 0.99, 1.35, 1.43 | | |
| MEK uptake 1D, 7D, 14D | 0.28, 0.65, 0.89 | 0.43, 0.67, 0.78 | | |
| JET FUEL uptake 1D, 7D, 14D | 0.11, 0.25, 0.38 | 0.26, 0.53, 0.73 | | |
| Shear Modulus GPa | | 4.39 +0.06 | | |

Notes on Table

Experimental bismaleimides used are described in PCT/AU93/00248.

In many cases values were determined for these parameters on several laminates. In these cases the value quoted is the average value obtained.

Tg is measured at 1 Hz in a Polymer Labs DMTA, Tb (point of break in Modulus) is given in parenthesis.

Values are averages where multiple determinations were available.

250° C. Stabilities are quoted as weight losses after 1, 7, 14 days.

204° C. Stabilities are quoted as weight losses after 1, 3 and 6 months.

We claim:

1. A curable resin formulation which comprises at least one monoallyloxyimide, diallyloxyimide or polyallyloxyimide of Formula 1:

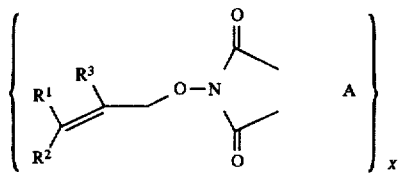

wherein:

X is an integer from 1 to 4 inclusive;

$R^1$, $R^2$, and $R^3$ are independently selected from the group consisting of hydrogen, alkyl, arylalkyl and halogen; and A is all or part of an aromatic, alicyclic or mixed aromatic/alicyclic ring system, optionally substituted with one or more alkyl, alkoxy, alkylthio, aryl, heteroaryl, aryloxy, carboxy, alkylamino, dialkylamino, amino, nitro, cyano, halo or haloalkyl groups.

2. A formulation as claimed in claim 1 which comprises at least one bismaleimide monomer.

3. A formulation as claimed in claim 1, wherein X=2 and A is part of a benzene ring or a fused aromatic system containing two or more aromatic rings, any of which may be optionally substituted.

4. A formulation as claimed in claim 1, wherein A is part of an optionally substituted aryl, bridged or bonded di- or poly-aryl or heteroaryl group.

5. A formulation as claimed in claim 1, wherein A is part of an optionally substituted alicyclic system.

6. A polyimide produced by curing a resin formulation as claimed in claim 1.

* * * * *